(12) United States Patent   (10) Patent No.: US 8,313,013 B2
Kuester, III et al.          (45) Date of Patent: Nov. 20, 2012

(54) METHOD AND ASSEMBLY FOR ANASTOMOSIS

(75) Inventors: William F. Kuester, III, Blaine, MN (US); Tracy Konobeck, Blaine, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 526 days.

(21) Appl. No.: 11/399,222

(22) Filed: Apr. 6, 2006

(65) Prior Publication Data

US 2007/0239180 A1    Oct. 11, 2007

(51) Int. Cl.
*A61B 17/11* (2006.01)

(52) U.S. Cl. .................. 227/175.1; 227/179.1; 227/19; 606/153

(58) Field of Classification Search .................. 606/153; 227/19, 175.1–182, 191
See application file for complete search history.

(56) References Cited

U.S. PATENT DOCUMENTS

| | | | |
|---|---|---|---|
| 1,151,300 A | 8/1915 | Soresi | 604/7 |
| 1,918,890 A | 7/1933 | Bacon | 606/155 |
| 2,434,030 A | 1/1948 | Yeomans | 606/153 |
| 2,453,056 A | 11/1948 | Zack | 606/153 |
| 2,638,901 A | 5/1953 | Sugarbaker | 606/153 |
| 3,155,095 A | 11/1964 | Brown | 606/154 |
| 3,191,842 A | 6/1965 | Fischer et al. | 227/155 |
| 3,254,650 A | 6/1966 | Collito | 606/153 |
| 3,254,651 A | 6/1966 | Collito | 606/153 |
| 3,258,012 A | 6/1966 | Nakayama et al. | 606/150 |
| 3,265,069 A | 8/1966 | Healey, Jr. et al. | 606/153 |
| 3,316,914 A | 5/1967 | Collito | 606/150 |
| 3,409,914 A | 11/1968 | Jones | 623/1.51 |
| 3,456,965 A | 7/1969 | Gajewski et al. | 285/260 |
| 3,484,121 A | 12/1969 | Quinton | 285/242 |
| 3,514,791 A | 6/1970 | Sparks | 623/213 |
| 3,552,626 A | 1/1971 | Astafiev | 227/76 |
| 3,561,448 A | 2/1971 | Peternel | 606/148 |
| 3,606,808 A | 9/1971 | Bowden | 82/165 |
| 3,606,888 A | 9/1971 | Wilkinson | 227/179.1 |
| 3,628,813 A | 12/1971 | Lee et al. | 285/31 |
| 3,648,295 A | 3/1972 | Palma | 600/36 |
| 3,683,925 A | 8/1972 | Frankel | 606/148 |

(Continued)

FOREIGN PATENT DOCUMENTS

CA          0899749       5/1972

(Continued)

OTHER PUBLICATIONS

Anastomoses of small vessels without sutures with the nakayama instrumentation, L. Leger et al., La Presse Medicale [The Medical Press], 72, No. 29, Jun. 13, 1964, p. 1657-1661, Paris, France (English translation of Anastomoses De Petits Vaisseaux Sans Sutures, Avec l'Instrumentation De Nakayama, La Presse Medicale, vol. 72, No. 29, Jun. 13, 1964, pp. 1657-1661).

(Continued)

*Primary Examiner* — Lindsay Low
(74) *Attorney, Agent, or Firm* — Bozicevic, Field & Francis LLP; Bret E. Field; Daniel G. Stoddard

(57) ABSTRACT

The invention includes an assembly for anastomosis having a clamp being arranged to support a fastener. The clamp can be actuated to join a vessel with the fastener to establish a fluid communication. In some embodiments, the invention includes an assembly having a clamp and a fastener with first and second joinable parts, and the assembly can be adapted to facilitate the alignment of the first and second joinable parts.

16 Claims, 15 Drawing Sheets

U.S. PATENT DOCUMENTS

| | | | |
|---|---|---|---|
| 3,683,926 A | 8/1972 | Suzuki | 606/154 |
| 3,713,441 A | 1/1973 | Thomas | 604/8 |
| 3,742,933 A | 7/1973 | Bucalo | 128/843 |
| 3,771,526 A | 11/1973 | Rudle | 606/153 |
| 3,774,615 A | 11/1973 | Lim et al. | 606/153 |
| 3,790,057 A | 2/1974 | Razgulov et al. | 227/19 |
| 3,831,584 A | 8/1974 | Bucalo | 128/843 |
| 3,833,940 A | 9/1974 | Hartenbach | 623/23.64 |
| 3,877,435 A | 4/1975 | Bucalo | 128/843 |
| 3,880,137 A | 4/1975 | Bucalo | 128/843 |
| 3,882,862 A | 5/1975 | Berend | 604/8 |
| 3,908,662 A | 9/1975 | Razgulov et al. | 606/149 |
| 3,945,052 A | 3/1976 | Liebig | 623/1.5 |
| 3,974,835 A | 8/1976 | Hardy | 606/154 |
| 3,990,434 A | 11/1976 | Free | 128/843 |
| 4,055,186 A | 10/1977 | Leveen | 606/153 |
| 4,076,162 A | 2/1978 | Kapitanov et al. | 227/19 |
| 4,198,982 A | 4/1980 | Fortner et al. | 227/179.1 |
| 4,200,107 A | 4/1980 | Reid | 128/843 |
| 4,214,586 A | 7/1980 | Mericle | 606/154 |
| 4,233,981 A | 11/1980 | Schomacher | 128/334 |
| 4,289,133 A | 9/1981 | Rothfuss | 227/175.3 |
| 4,294,255 A | 10/1981 | Geroc | 606/153 |
| 4,306,545 A | 12/1981 | Ivan et al. | 128/887 |
| 4,331,150 A | 5/1982 | Braun et al. | 606/150 |
| 4,350,160 A | 9/1982 | Kolesov et al. | 227/179.1 |
| 4,449,531 A | 5/1984 | Cerwin et al. | 606/158 |
| 4,467,802 A | 8/1984 | Maslanka | 606/206 |
| 4,487,205 A | 12/1984 | Di Giovanni et al. | 606/158 |
| 4,505,272 A | 3/1985 | Utyamyshev et al. | 227/179.1 |
| 4,523,592 A | 6/1985 | Daniel | 606/153 |
| 4,607,637 A | 8/1986 | Berggren | 128/334 |
| 4,624,257 A | 11/1986 | Berggren | 128/334 |
| 4,917,090 A | 4/1990 | Berggren | 606/153 |
| 4,917,091 A | 4/1990 | Berggren | 606/153 |
| 5,250,058 A | 10/1993 | Miller et al. | |
| 5,562,690 A | 10/1996 | Green et al. | |
| 2001/0016749 A1 | 8/2001 | Blatter et al. | |
| 2002/0058955 A1 | 5/2002 | Blatter et al. | |

FOREIGN PATENT DOCUMENTS

| | | |
|---|---|---|
| CA | 0908529 | 8/1972 |
| DE | 1057729 | 5/1959 |
| DE | 1303833 | 8/1963 |
| DE | 2101282 | 7/1972 |
| DE | 2101284 | 7/1972 |
| DE | 2200981 | 7/1973 |
| DE | 2600142 | 7/1977 |
| DE | 2657255 | 6/1978 |
| FR | 2316910 | 2/1977 |
| GB | 1181563 | 2/1970 |
| GB | 1321391 | 6/1973 |
| WO | WO 82/01644 | 5/1982 |
| WO | WO9830153 A1 | 7/1998 |

OTHER PUBLICATIONS

The anastomosis of arteries of very small diameter using the Nakayama anastomotic button, P. Replumaz et al., Surgical Society of Lyon, 60, p. 263-270, 1964 (English translation of "L'anastomosose des arteres de tres petite diametre a l'aide du bouton anastomotique de Nakayama", P. Replumaz et al, Lyon Chir 60, 263 (1964).

EP Application No. 071056477, European Search Report, Jun. 4, 2010, pp. 1-6, European Patent Office, Munich, Germany.

Holt et al., "A New Technique for End-to-End Anastomosis of Small Arteries", Surgical Forum 11:242 (1960).

Nakayama et al., "A Simple New Apparatus for Small Vessel Anastomosis (Free Autograft of the Sigmoid Included)", Surgery, vol. 52, No. 6, pp. 918-931 (Dec. 1962).

"Extended Laryngopharyngectomy for Carcinoma of the Laryngopharynx and the Cervical Oesophagus (Use of a Free Graft of Large Intestine)", P. Chrysospathis et al, J. Laryngol 79, 233-236 (1965).

"Internal Mammary-Coronary Artery Anastomoses, A Method Utilizing Nakayama's Instrument for Small Vessel Anastomoses", Koki Abe, M.D. et al, J. Thorac Cardiovsc Surg 51, 808-820 (1966).

"Observations on the Technique of Microvascular Anastomosis Using the Nakayama Instrument", R. B. Bradshaw, M.D. et al, Proc. Can Otolaryng. Soc., 23, 1969, pp. 96-105.

"A New Vascular Anastomosing Instrument and Its Clinical Application", Komei Nakayama M.D. et al, Clin Ortho Rel Res 29, 123-131 (1963).

"Unilink Instrument System for Fast and Safe Microvascular Anastomosis", Leif T. Ostrup M.D., The Unklink Company, 1986.

"Anastomosis of Small Veins With Suture or Nakayama's Apparatus, A Comparative Study", Leif T. Ostrup, Scand J. Plast Reconstr. Surg., 10:9-17, 1976.

"Microvascular Surgery, Techniques and Applications in Plastic Surgery", Leif T. Ostrup et al, Scand J. Plast Reconstr. Surg. 10:18-28, 1976.

METHOD AND ASSEMBLY FOR ANASTOMOSIS

TECHNICAL FIELD

The invention relates to a method and assembly for anastomosis.

BACKGROUND OF THE INVENTION

Anastomosis is the joining of two vessels together to establish fluid communication between them. One approach to accomplish this coupling has been to provide a surgical instrument having a clamp carrying a fastener. In such instruments the clamp generally has two members, each carrying a portion of the fastener that pivots towards each other to close the fastener. In many embodiments, each portion of the fastener includes a ring having axially directed pins and corresponding pin receiving holes. Such an approach to anastomosis has been described in Applicant's own U.S. Pat. Nos. 4,607,637, 4,624,257, 4,917,090, and 4,917,091, the disclosures of which are hereby incorporated by reference. Unfortunately, as the ring and/or pin size increases it becomes more difficult to align the pins with their corresponding holes on the opposite fastener piece because of the angles produced in the pivoting closure movement. This restriction can result in the use of smaller than optimum ring sizes and/or larger tools that are cumbersome in a surgical area.

SUMMARY OF THE INVENTION

The invention provides a method, an assembly, and various assembly components as described herein useful for joining two vessel ends and establishing a liquid connection between them, i.e., anastomosis. For example, the assembly can be used for end-to-end vessel anastomosis, end-to-side anastomosis and arterial/venous interpositional vein grafts. The size of the vessels that can be joined with some embodiments of the assembly range from about one half millimeter (mm) to about 5 mm or larger in outer diameter.

The invention provides an assembly for anastomosis. In a preferred embodiment the assembly comprises a clamp and a fastener having first and second joinable parts carried by the clamp. The assembly is adapted to position the fastener parts at a desired location within the body, and in turn, to facilitate the alignment of the fastener parts in the course of coupling them to form the anastomotic joint. By "facilitate the alignment" it is generally meant that the assembly can be used to position and move the first and second joinable parts with respect to each other in a manner that permits them to be coupled in a predetermined and optimal manner, given their respective structures and dimensions.

The apparatus is particularly well suited for fasteners in which the first and second joinable parts each have a disc-type shape with a plurality of axially directed pins and a corresponding plurality of receiving apertures distributed on a circumference around the disc, as generally described in the above-referenced patents. With such fasteners, the receiving apertures of the first joinable part can be sized to a dimension of the pins of the second joinable part, and vice versa, so as to form a forced fit between each pin and its corresponding apertures, in order to securely join the parts themselves together. In such embodiments, the assembly of this invention permits the use of joinable parts having larger diameters and/or longer pins than those presently available, since the assembly permits the pins and corresponding apertures to be positioned in a substantially axial relationship at the time of coupling essentially regardless of the manner or angle at which the clamp portions of the clamp carrying the respective parts may approach each other. By contrast, conventional clamps and fasteners have generally relied upon the use of relatively smaller diameter parts, or smaller pins, or both, such that the parts could be coupled with little concern for the contacting angle between the parts themselves.

An apparatus of this invention permits the opposing faces of both fastener parts to be positioned substantially parallel to each other at the point of contact, in turn, such that their respective apertures and pins can be generally aligned in an axial manner upon closure. The apparatus can achieve this result in any suitable manner, relying on any combination of the relative movement of the first and second parts toward each other, and/or the configuration of the clamp with respect to the fastener parts, and/or the relative sizes, shapes, and/or configurations of the fastener parts themselves.

In one embodiment, for instance, (1) the apparatus provides for movement of the respective parts toward each other at a predetermined angle relative to the clamp. In an alternative embodiment, (2) the respective joinable parts are themselves provided with varying thickness to permit substantial alignment of their opposing faces at the time of closure. In yet another alternative embodiment, (3) the apparatus is adapted to move the corresponding parts in a substantially parallel manner in the course of their coupling (e.g., translational movement). Yet other embodiments can include aspects of some or all of these approaches.

The assembly is particularly well suited for use in aligning first and second joinable parts that, given the relative position and dimensions of the parts and their pins, would otherwise not be suitably aligned if provided upon and closed by a conventional pivoting clamp. The present assembly thereby permits larger joinable parts and/or longer pins to be held by a single clamp, yet manipulated in a surgical fashion to permit the parts to align at an appropriate time.

Such an assembly allows for the use of a greater range of fastener sizes, including both fastener diameter, pin length, and pin diameter. The greater range of fastener sizes allows for the optimization of the fastener size with respect to the application. In addition, the assembly allows the use of larger fasteners without unnecessarily increasing the size of the overall assembly, thereby making the assembly amenable for use in the surgical site.

Other embodiments of the invention include various aspects of the assembly. For example, in some embodiments the invention includes an assembly having a clamp adapted to hold a fastener part at an angle relative to the clamp, but does not include the fastener per se. In yet other embodiments, the invention includes a fastener with joinable parts provided with varying thickness to permit substantial alignment of their opposing major faces at the time of closure, but does not include the remainder of the assembly per se. Further, some embodiments of the invention include a vessel coupled together by an anastomotic joint provided in the manner described herein.

The invention also includes a method of making an assembly of this invention, and its various component parts, as well as a method of using the assembly of this invention to create an anastomotic joint. In use, for example, the severed end of a vessel can be threaded through an aperture within a first joinable part of a fastener. Another severed end of a vessel can be threaded through a second joinable part of the fastener. Each vessel end can then be anchored to its respective joinable part by directing pins carried by the joinable part through the vessel. Either or both joinable parts can be received within the clamp before or after the corresponding vessel is threaded and anchored. Once positioned in the clamp, with the vessels attached, the assembly can then be activated to move the two joinable parts towards each other. In some embodiments, the assembly is adapted to facilitate the alignment of the joinable parts as described herein. Once the joinable parts meet, the pins of one joinable part can align with the receiving apertures of the opposite joinable part. Continued actuation of the assembly will cause the joinable parts to join and the anastomosis will be complete. The fastener can then be removed from the clamp and the assembly can be removed from the surgical area.

DETAILED DESCRIPTION OF THE INVENTION

The following detailed description should be read with reference to the figures, in which like elements in different drawings are numbered identically. The figures, which are not necessarily to scale, depict selected embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

The invention provides a method and assembly for anastomosis. In some embodiments, the assembly includes a clamp and a fastener having first and second joinable parts, and the assembly can be adapted to facilitate the alignment of the first and second joinable parts. Such facilitation of alignment allows for the use of optimum sized fasteners without unnecessarily or unduly increasing the size of the overall assembly.

Figure 1:
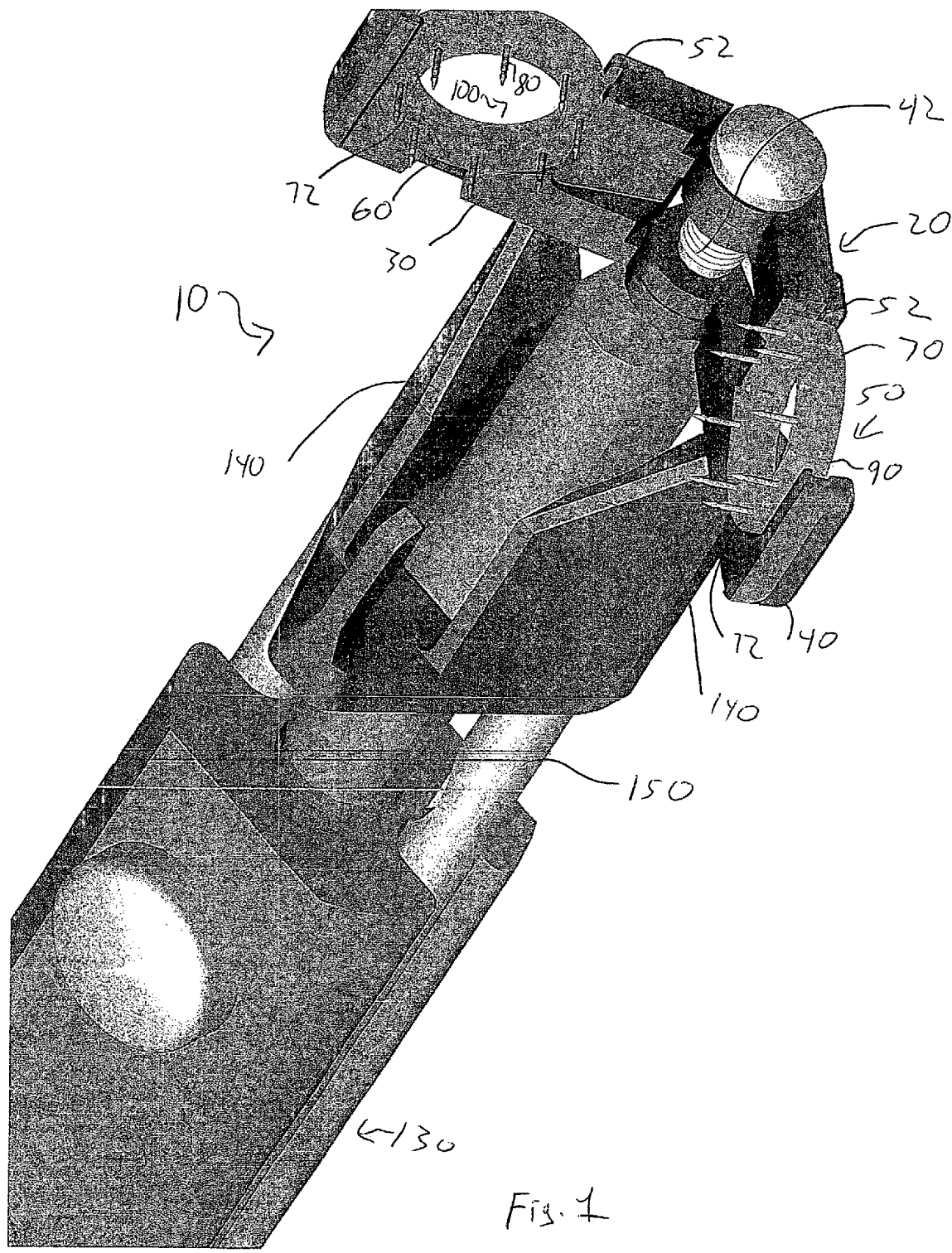
FIG. 1 provides a perspective view of an assembly in accordance with an embodiment of the invention.

FIG. 1 illustrates an assembly of the invention useful for joining two vessels with a fastener. As will be further described herein, the assembly is adapted to facilitate the alignment of two joinable parts of a fastener to more efficiently perform an anastomosis.

In the embodiment of FIG. 1 the assembly 10 includes a clamp 20. Clamp 20 can comprise any suitable feature, such as a first clamp portion 30 and a second clamp portion 40. A carrier rod 42 that generally follows the longitudinal axis of the assembly 10 can support first and second clamp portions 30, 40. For example, the first and second clamp portions 30, 40 can be hingedly connected to the assembly 10. In some embodiments, the clamp 20 is adapted to support a fastener 50. For example, the clamp can contain one or more slots 52 useful for receiving a fastener 50. In some embodiments, the slot 52 can include a guide element useful for orientating the fastener within the slot 52.

The fastener 50 can comprise any suitable structure for joining two ends of a vessel together. In some embodiments, the fastener 50 includes a first joinable part 60 and a second joinable part 70. In such embodiments, first joinable part 60 can be carried by first clamp portion 30 and second joinable part 70 can be carried by second clamp portion 70.

The joinable parts 60, 70 can themselves comprise any suitable feature useful to allow them to join together and establish a fluid communication between the two vessels. In some embodiments, each joinable part 60, 70 can include a generally disc-type shape having an opposing face 72 and a plurality of pins 80 and receiving apertures 90 sized and shaped to receive a corresponding pin circumferentially disposed around the disc. The pins and corresponding receiving apertures can be equally circumferentially spaced around the disc. In some embodiments, the disc can have a diameter of more than about 3.5 millimeters (mm), and in other embodiments can have a diameter of more than about 4 mm. In yet other embodiments the disc can have a diameter of more than about 5 mm (e.g., up to about 10 mm). Further, in some embodiments the distance from the center of the disc to the carrier rod 42 is between about 2 mm and about 10 mm. In some embodiments the distance from the center of the disc to the carrier rod 42 is between about 3 mm and about 7 mm (e.g., about 3.81 mm and about 6.35 mm). In embodiments where the joinable parts 60, 70 pivot towards each other, such discs can create large angles between the joinable parts 60, 70.

The disc can include a disc aperture 100, and, in some embodiments, disc aperture 100 can be generally centrally located within the disc. In such embodiments, the ends of the vessels that are desired to be joined can be attached to the fastener 50. For example, the ends of the vessels can be threaded through the disc aperture 100 and anchored onto the pins 80. The joinable parts 60, 70 can then be joined to establish fluid communication (e.g., blood flow) between the two vessels.

In embodiments of the joinable parts 60, 70 having one or more pins 80, the pin 80 can include any shape suitable for mating with receiving aperture 90. For example, pin 80 can include a generally elongate member. Further, any number of pins 80 can be provided. In some embodiments, eight or more pins 80 (and a corresponding number of receiving apertures 90) are provided on each joinable part 60, 70. The pins can have any suitable diameter and exposed length. For example, the pins can have a diameter of up to about 0.05 mm. In some embodiments, the pin can have a diameter of about 0.015 mm. In other embodiments, the pins have a diameter of about 0.0175 mm. In yet other embodiments, the pins have a diameter of about 0.02 mm. Further, the pins can have an exposed length of up to about 2 mm. In some embodiments, the pins have an exposed length of about 0.9 mm. In other embodiments, the pins have an exposed length of about 1.2 mm. In yet other embodiments, the pins have an exposed length of about 1.4 mm.

In some embodiments, the assembly 10 includes a fastener 50 with first and second joinable parts 60, 70, each part having a disc-type shape with a plurality of pins 80 and receiving apertures 90 distributed on a circumference around the disc. The receiving apertures 90 of the first joinable part 60 can be sized to a dimension of the pins 80 of the second joinable part 70, and vice versa, so as to form a forced fit when the joinable parts 60, 70 are joined. In such embodiments, the assembly 10 can be adapted to facilitate the alignment of the first and second joinable 60, 70 parts of the fastener 50 by facilitating the alignment of the pins and receiving apertures.

In some embodiments, the assembly 10 can include a clamp 20 and a fastener 50 with first and second joinable parts 60, 70, and the assembly 10 can be adapted to facilitate the alignment of the first and second joinable parts. For example, the assembly can be adapted to reduce the angle between the first and second joinable parts 60, 70 as they move towards each other, including reducing the angle towards zero degrees and having the first and second joinable parts translate towards each other.

The assembly 10 can be adapted to facilitate the alignment of the first and second joinable parts 60, 70 in any suitable manner that orientates the opposing faces of the joinable parts in a substantially parallel configuration at the point of mating the two joinable portions, such as, for example, at the point where the tips of the pin 80 first contact its corresponding receiving aperture 90. For example, the clamp 20 can be adapted to facilitate the alignment of the first and second joinable parts 60, 70, such as by holding one or more of the first and second joinable parts at an angle relative to the clamp. In other embodiments, one or more of the first and second joinable parts include a varying thickness to promote alignment. In yet other embodiments, the assembly can have dual plane clamps. Other embodiments include assemblies having more than one of these features to facilitate alignment.

The present invention provides an assembly for anastomosis employing a clamp and a fastener having first and second joinable parts carried by respective first and second clamp portions of the clamp, wherein the joinable parts each provide a respective opposing face providing pins extending axially therefrom and receiving apertures adapted to be mated axially with corresponding pins from the other opposing face. By means of comparison to clamps previously known, the respective diameters of the opposing faces and pin lengths being such that the joinable parts cannot be suitably aligned if positioned upon a clamp having straight clamp portions joined by a simple pivot point located between about 2 mm to about 10 mm from the center of the faces. Instead, it is by virtue of the present invention that Applicant provides an assembly that is nevertheless adapted to align and join the joinable parts.

Figure 2:
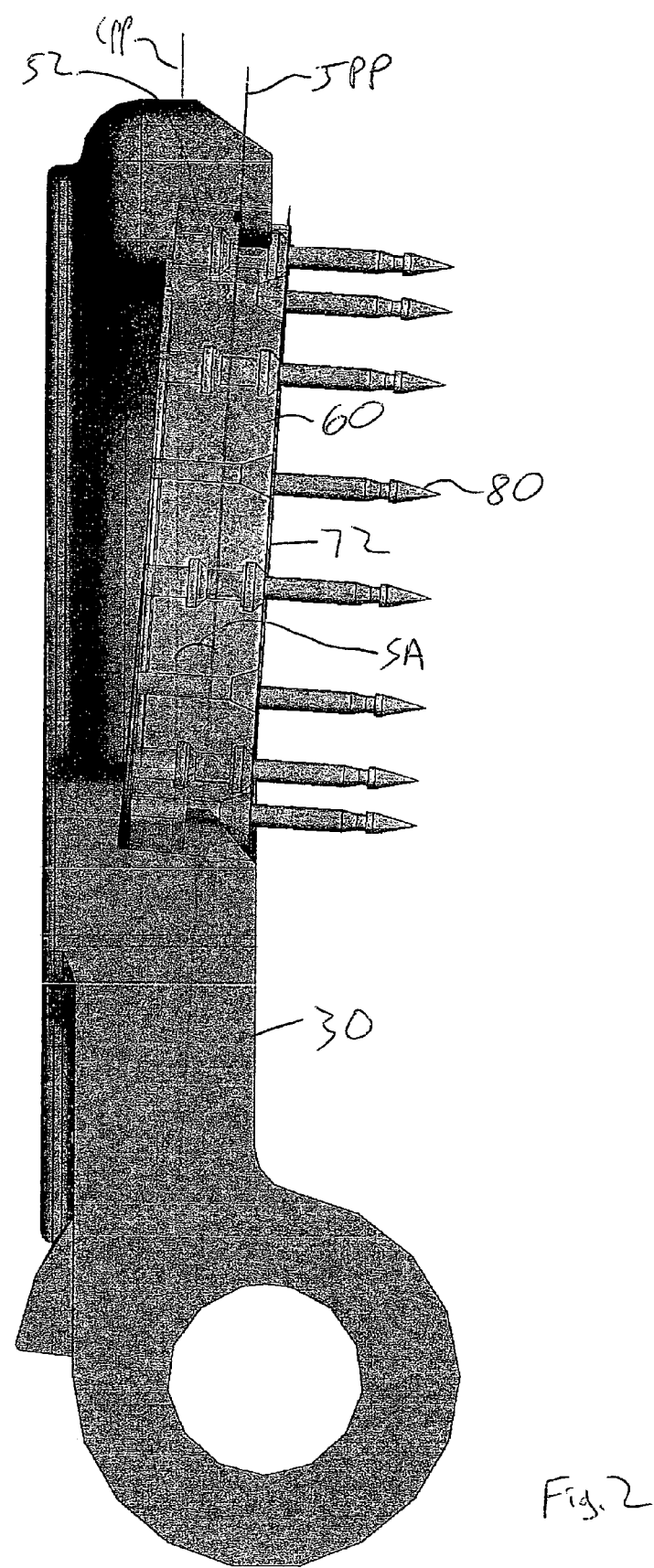
FIG. 2 provides a top plan view of a clamp and fastener in accordance with an embodiment of the invention.
Figure 3:
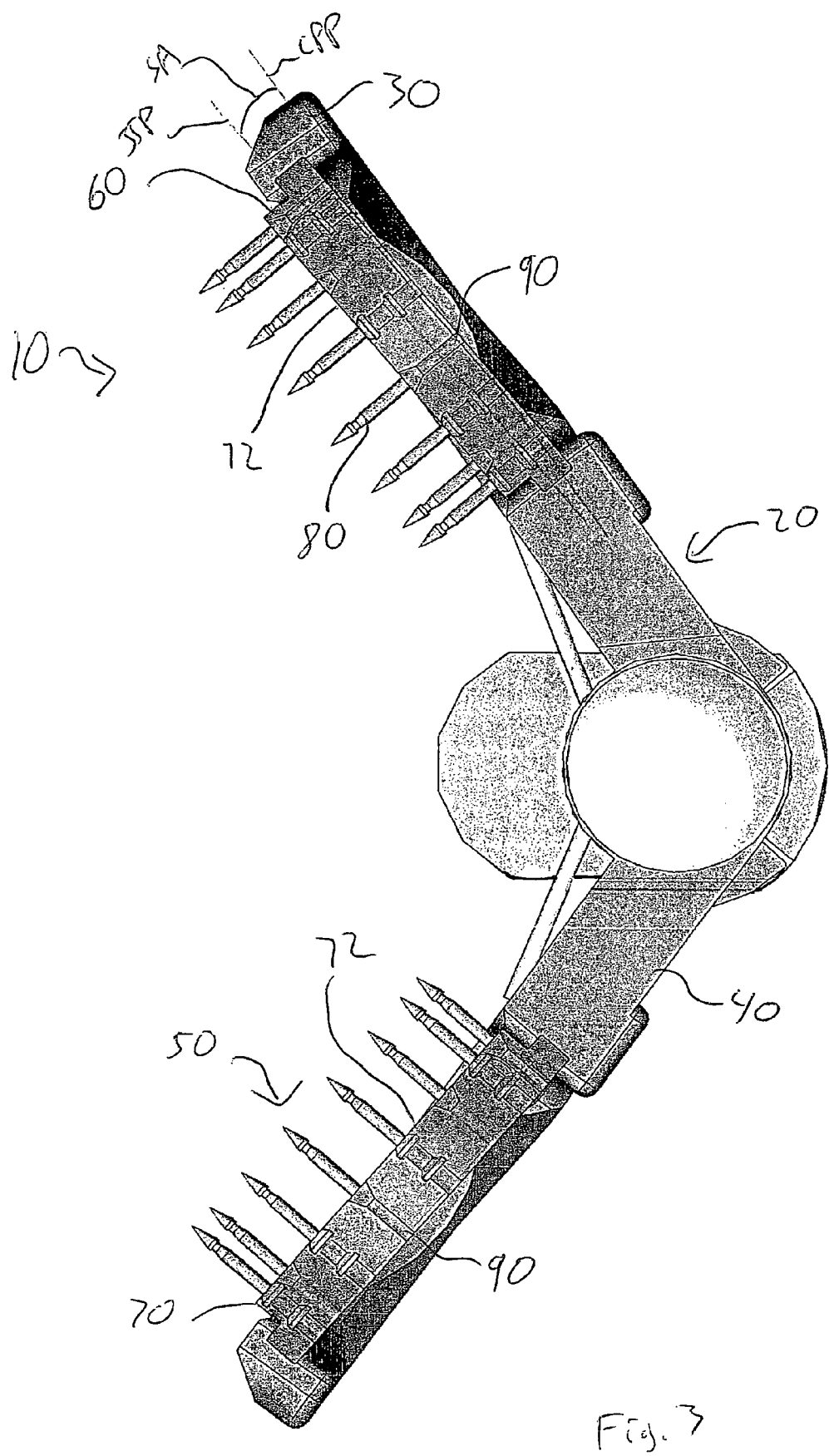
FIG. 3 provides a top plan view of an assembly in accordance with an embodiment of the invention.
Figure 4:
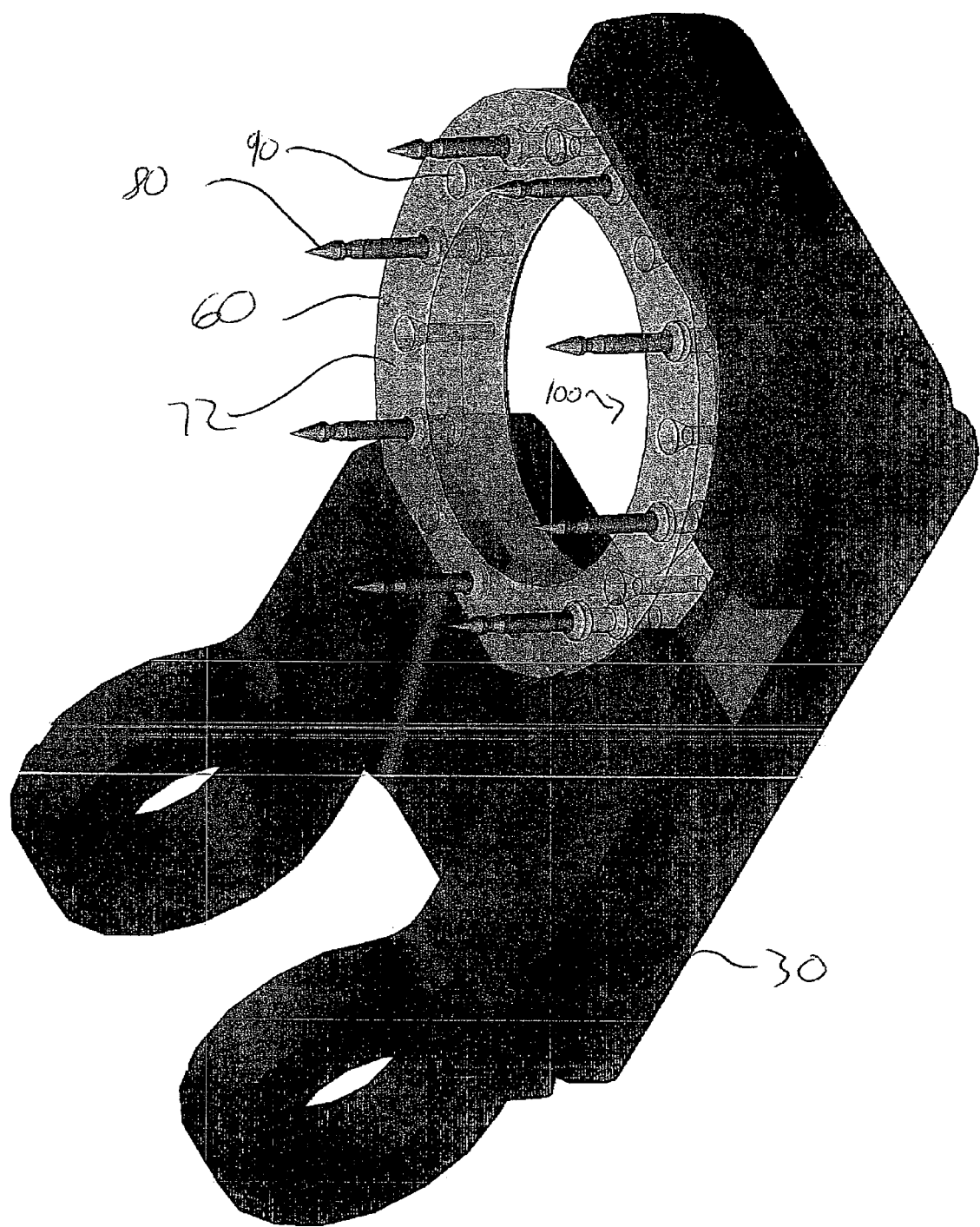
FIG. 4 provides a front perspective view of a clamp and fastener in accordance with an embodiment of the invention.
Figure 5:
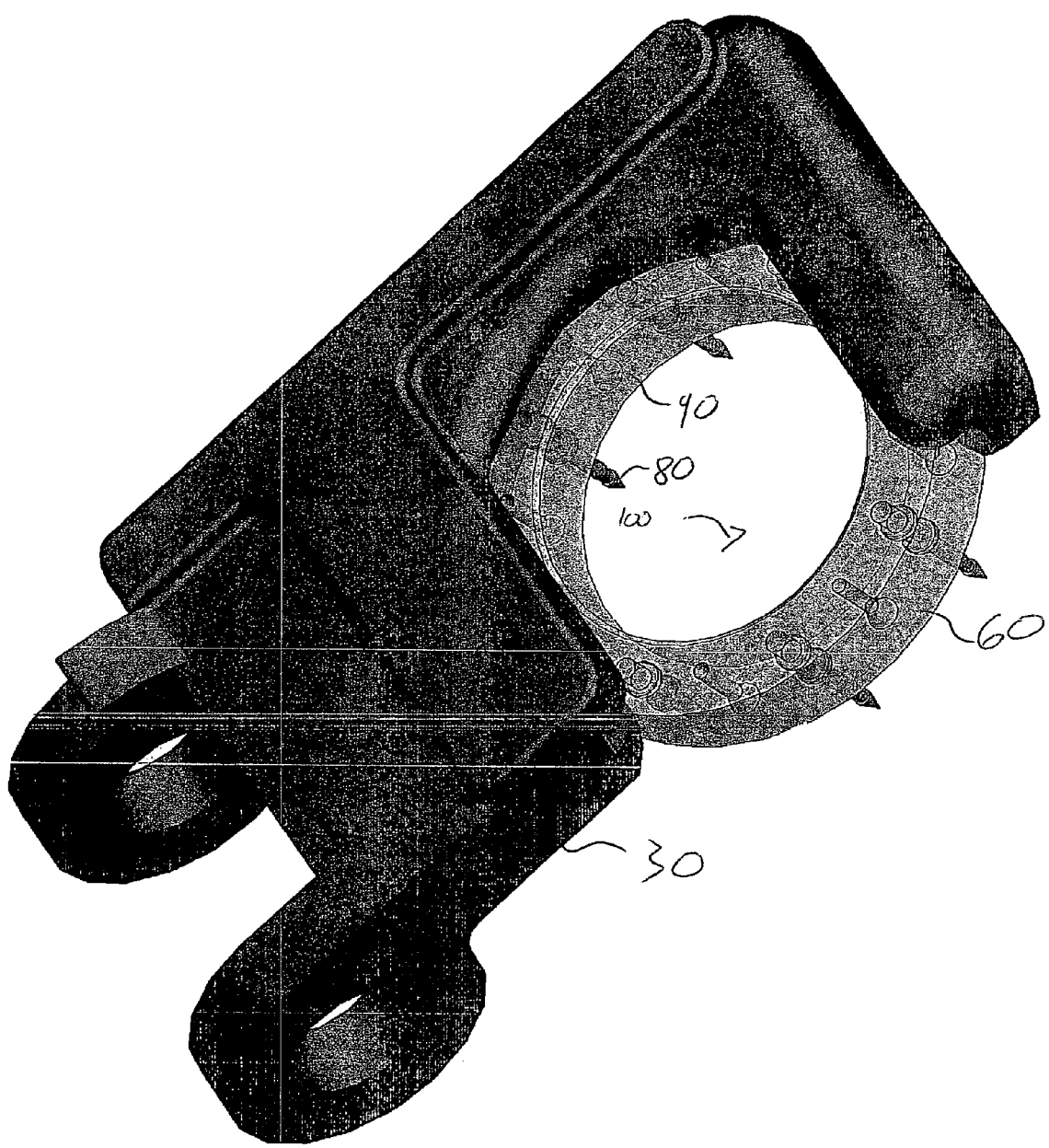
FIG. 5 provides a rear perspective view of a clamp and fastener in accordance with an embodiment of the invention.
Figure 6:
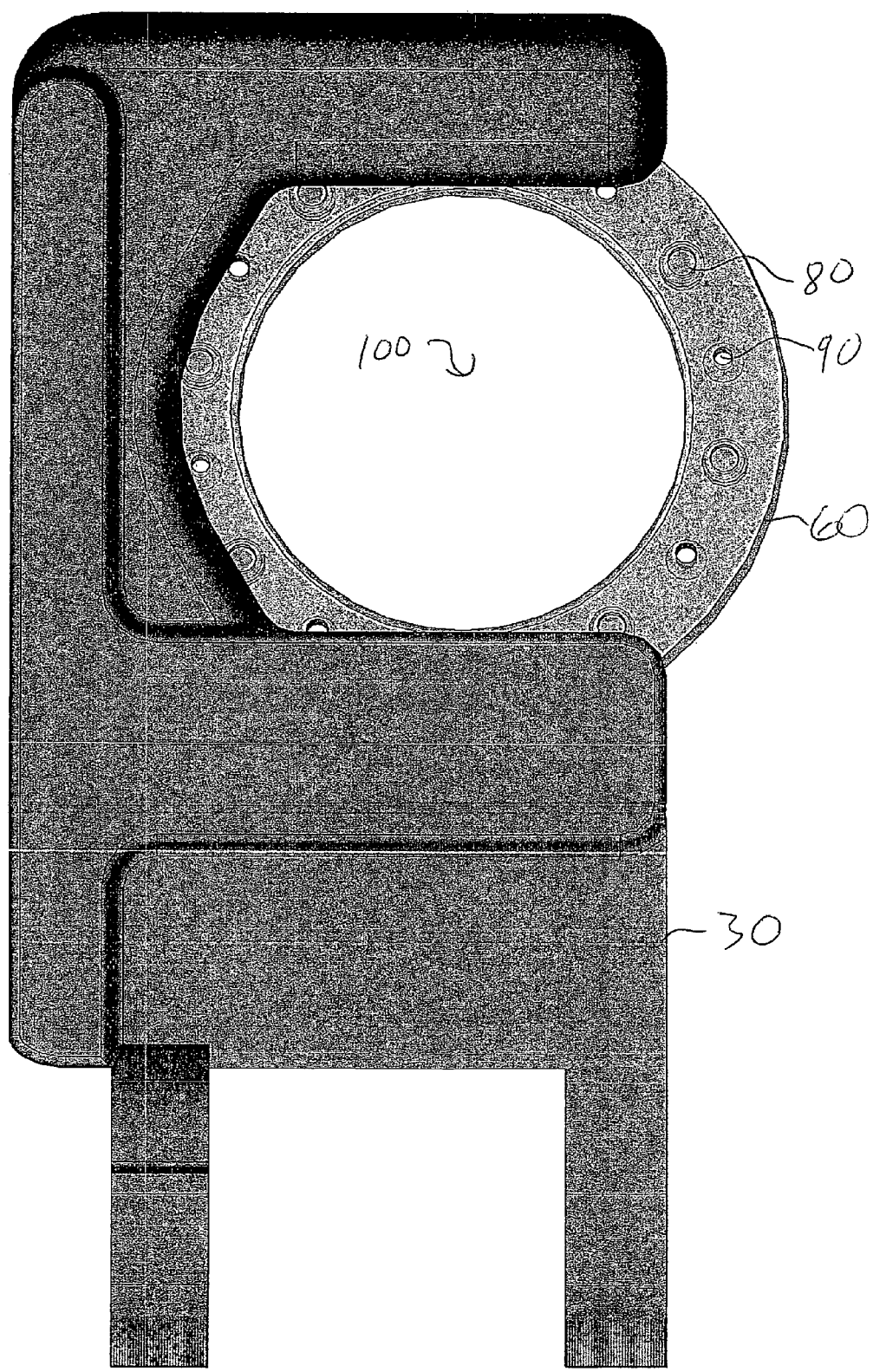
FIG. 6 provides a rear plan view of a clamp and fastener in accordance with an embodiment of the invention.

FIGS. 2-7 show various views of clamps 20 can be adapted to facilitate the alignment of the first and second joinable parts 60, 70 by holding the first and second joinable parts at an angle. As shown in FIGS. 2 and 3, each of the first and second clamp portions 30, 40 can have a clamp portion plane CPP. In addition, each of the first and second joinable parts 60, 70 can have a joinable part plane JPP. In some embodiments, the clamp portion plane CPP and the joinable part plane JPP are skewed relative to each other so as to facilitate alignment, as shown in FIGS. 2 and 3. Further, angle SA can be defined as the angle between the clamp portion plane CPP and the joinable part plane JPP, as shown in FIGS. 2 and 3. Angle SA can be of any magnitude to facilitate alignment. In some embodiments, angle SA is more than about one degree. In other embodiments, angle SA is more than about three degrees. In yet other embodiments, angle SA is more than about 5 degrees. In yet other embodiments, angle SA is more than about 7 degrees. In yet other embodiments, angle SA is about 10 degrees. The magnitude of the angle SA can depend on one or more of the distance between the joinable parts and the pivot point joining planes CPP, the size of the joinable parts 60, 70, the size and number of pins 80, if included, the method by which the joinable parts are brought together, the relative diameters of pins and corresponding apertures, and the particular application.

Figure 8:
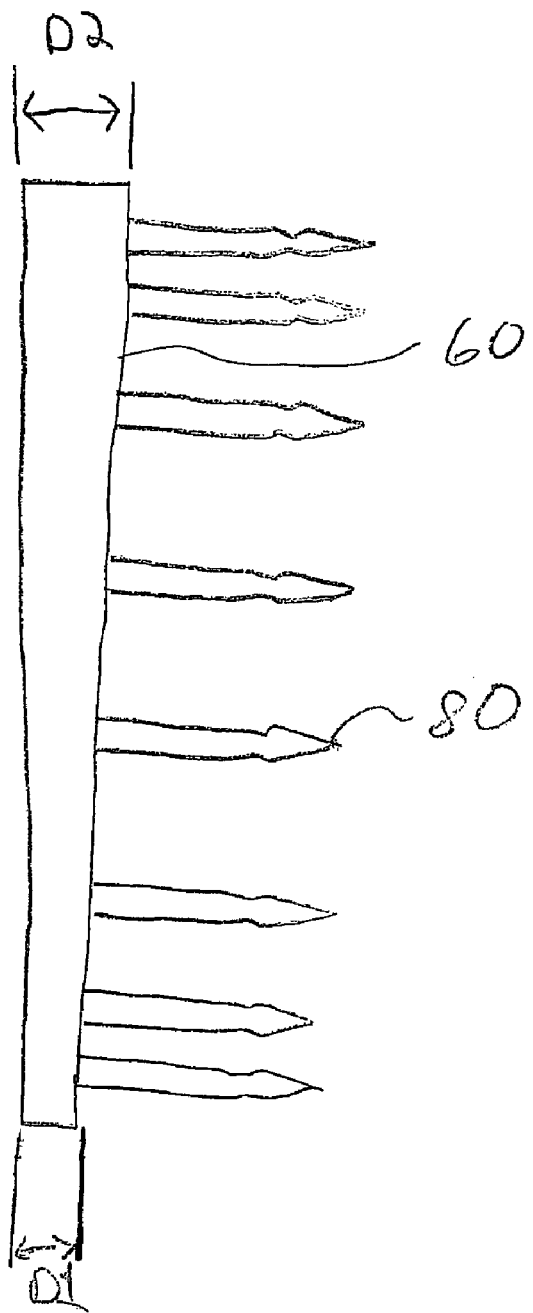
FIG. 8 provides a top plan view of a fastener in accordance with an embodiment of the invention.

In other embodiments, one or more of the first and second joinable parts 60, 70 include a varying thickness to promote alignment, as shown in FIG. 8. In such embodiments, the joinable part can have a first thickness D1 at a first location, such as proximate the carrier rod 42. The joinable part can also have a second thickness D2 at a second location, such as distal of the carrier rod 42. In some embodiments, the second thickness D2 is greater than the first thickness D1. The varying thickness can provide the desired angle SA between the clamp portion plane CPP and the joinable part plane JPP as described above. Such a configuration reduces the angle between the first and second joinable parts 60, 70 and thereby facilitates alignment.

Figure 9:
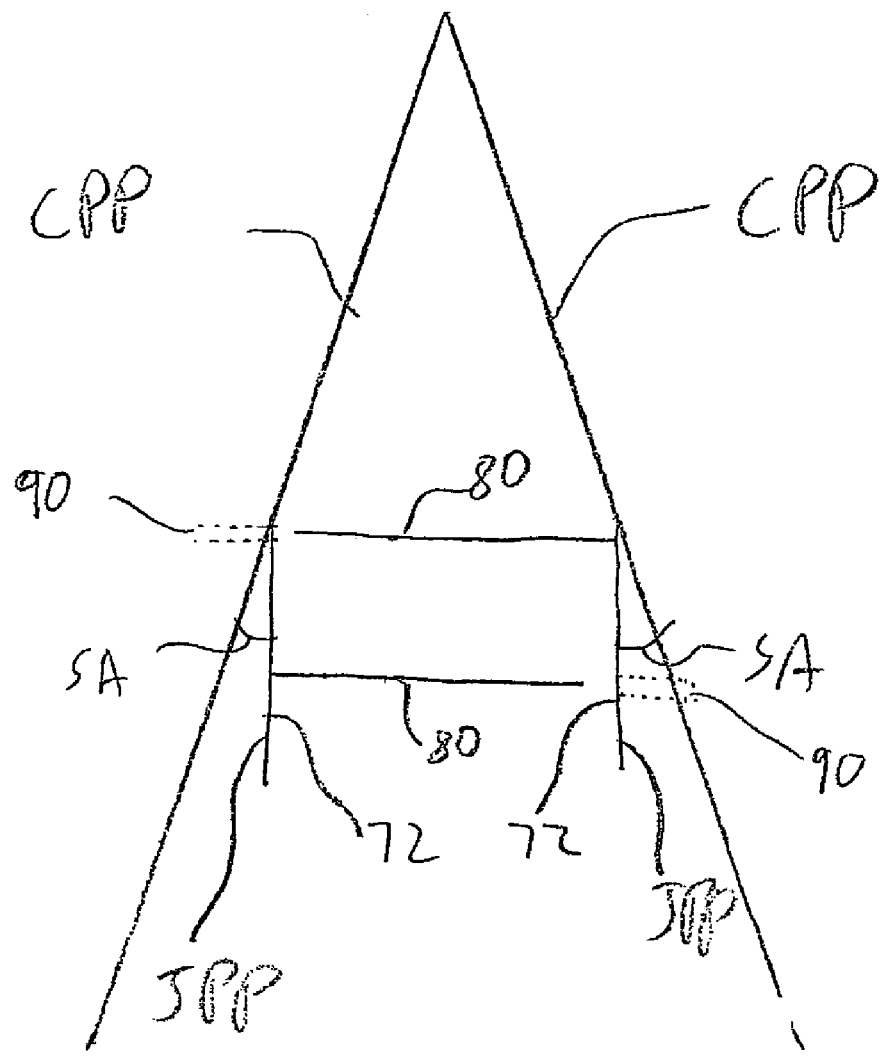
FIG. 9 provides a schematic representation of a geometric configuration of an assembly in accordance with an embodiment of the invention.
Figure 10:
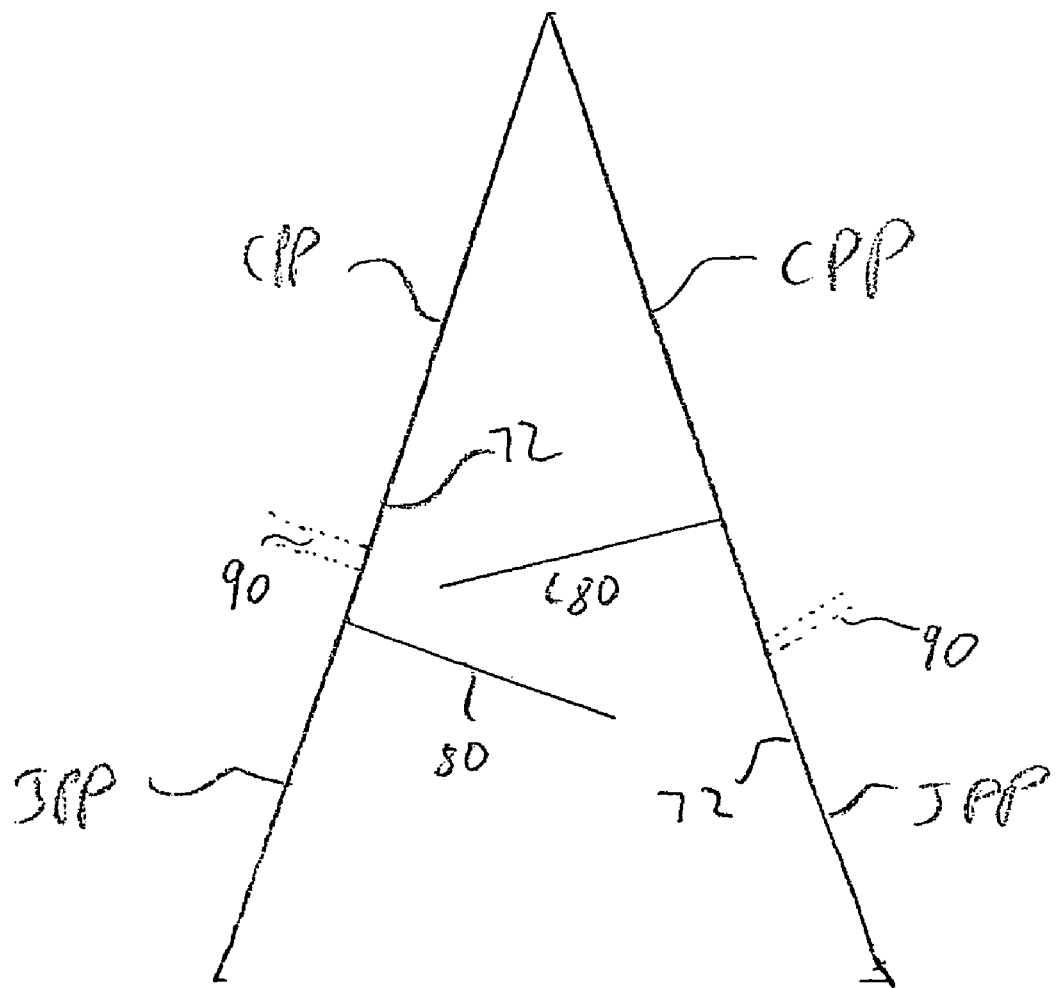
FIG. 10 provides a schematic representation of a prior art device.

The geometric relationship between the clamp portion plane CPP and the joinable part plane JPP are represented schematically in FIGS. 9 and 10. FIG. 9 shows an exaggerated schematic geometric relationship in accordance with an embodiment of the invention, and FIG. 10 shows an exaggerated representative schematic geometric relationship of a prior art device having approximately the same general size. As shown in FIG. 9, embodiments of the invention that include an angle SA between the clamp portion plane CPP and the joinable part plane JPP, whether by the clamp portion holding the joinable part at an angle or by providing a joinable part with varying thickness, facilitates the alignment of the joinable portions of the fastener by allowing the opposing faces of the joinable parts to be substantially parallel at the point where the tips of the pin 80 first contact its corresponding receiving aperture 90 (not depicted in FIGS. 9 and 10). In contrast, prior art devices with approximately sized clamp portions and pin size that rely on an unmodified pivoting action will not align and the joinable parts will not be able to join, as shown in FIG. 10.

Figure 11:
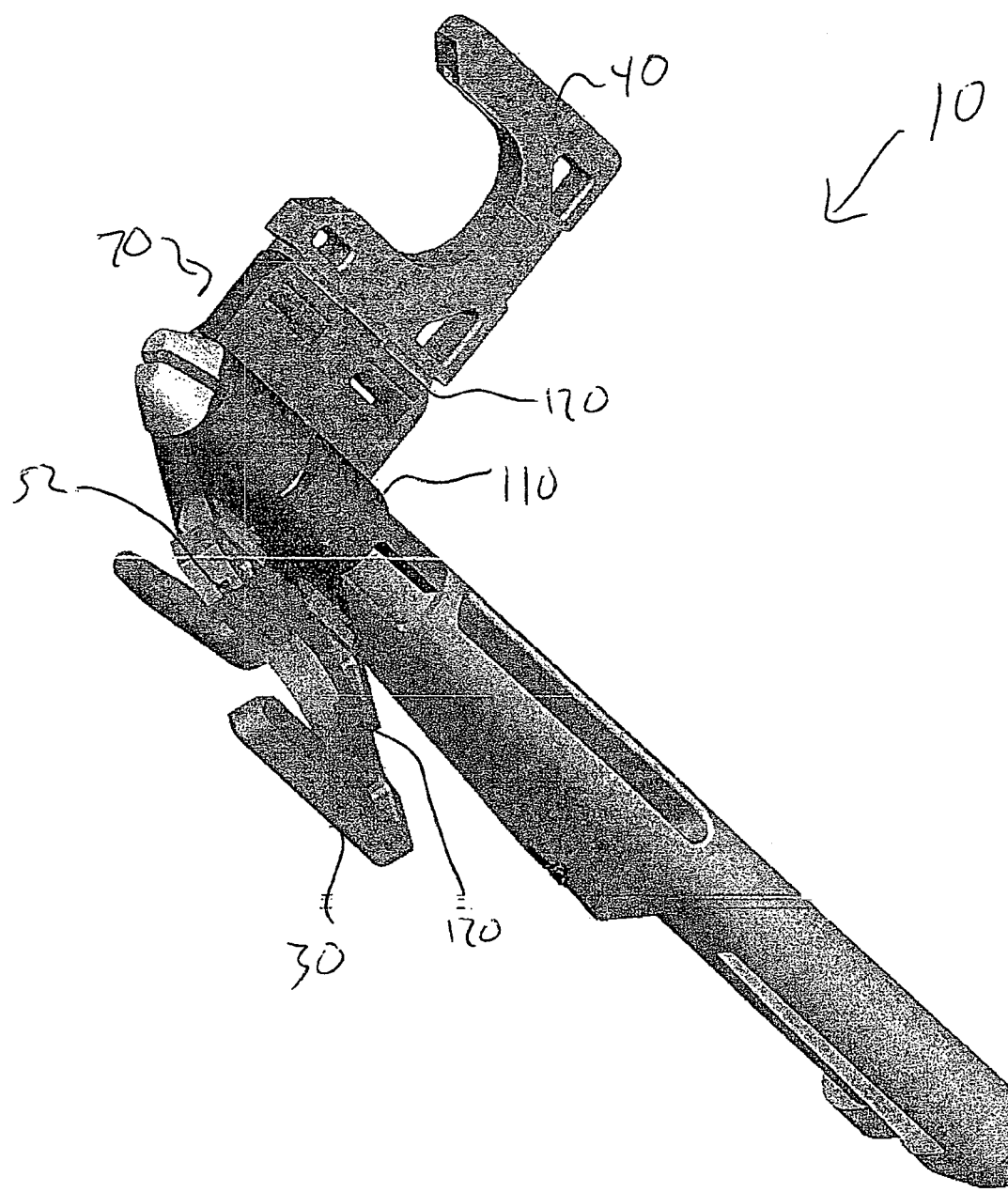
FIG. 11 provides a perspective view of an assembly in accordance with an embodiment of the invention.
Figure 12:
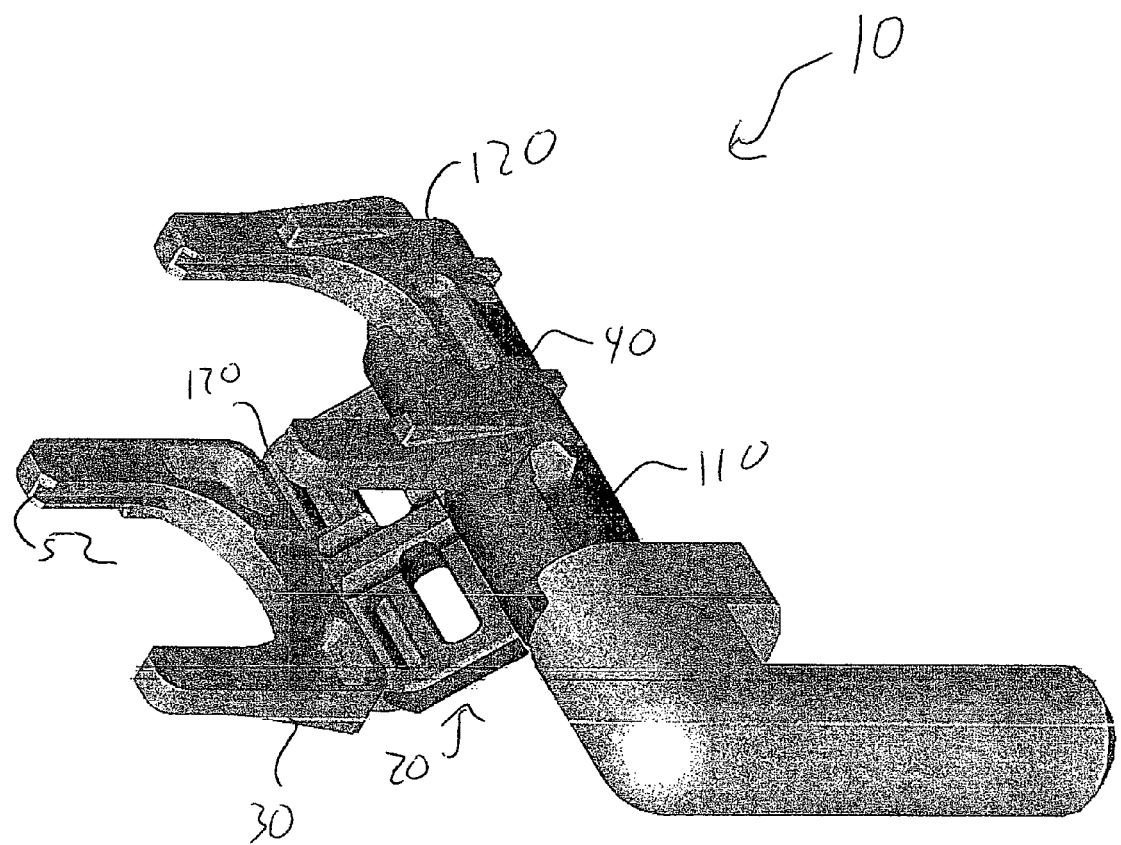
FIG. 12 provides a perspective view of an assembly in accordance with an embodiment of the invention.

As shown in FIGS. 11-12, in some embodiments the assembly 10 can have dual plane clamps. In such embodiments, one or more of the first and second clamp portions 30, 40 can have a first hinge 110 and a second hinge 120. Such embodiments allow the first and second joinable parts 60, 70 respectively held within the first and second clamp portions 30, 40 to translate towards each other to facilitate alignment. Such a dual plane clamp assembly allows the first and second joinable portions of the fastener to approach each other in a parallel relationship, thereby facilitating alignment of the pins and corresponding receiving apertures.

In other embodiments, the assembly 10 can have more than one of the features discussed herein. For example, the clamp 20 can be adapted to facilitate the alignment of the first and second joinable parts 60, 70, such as by holding one or more of the first and second joinable parts at an angle and one or more of the first and second joinable parts can include a varying thickness to promote alignment. In yet other embodiments, the assembly can have dual plane clamps and one or more of the clamp 20 adapted to facilitate the alignment of the first and second joinable parts 60, 70, such as by holding one or more of the first and second joinable parts at an angle and one or more of the first and second joinable parts can include a varying thickness to promote alignment.

Figure 13:
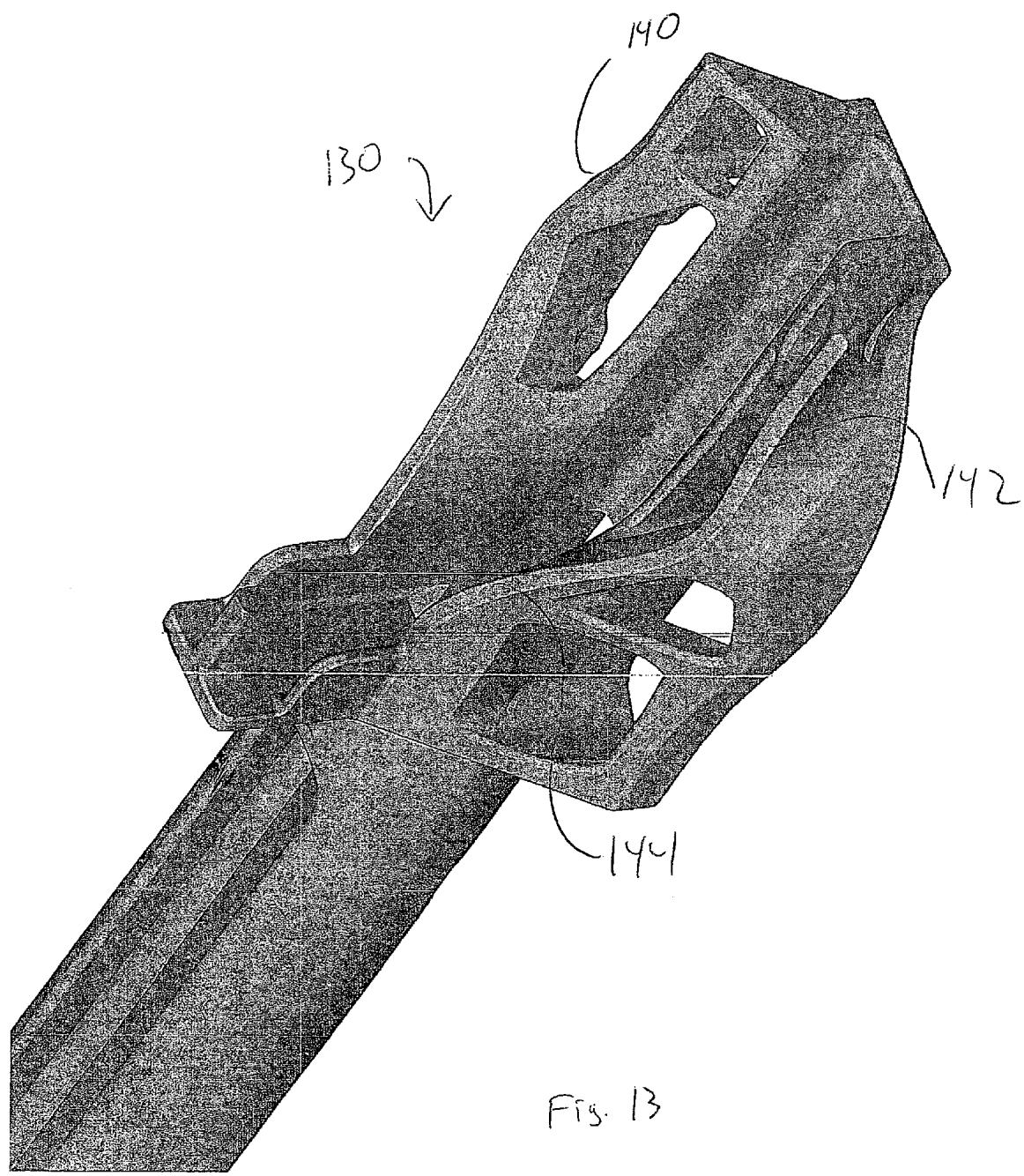
FIG. 13 provides a perspective view of an actuator in accordance with an embodiment of the invention.
Figure 14:
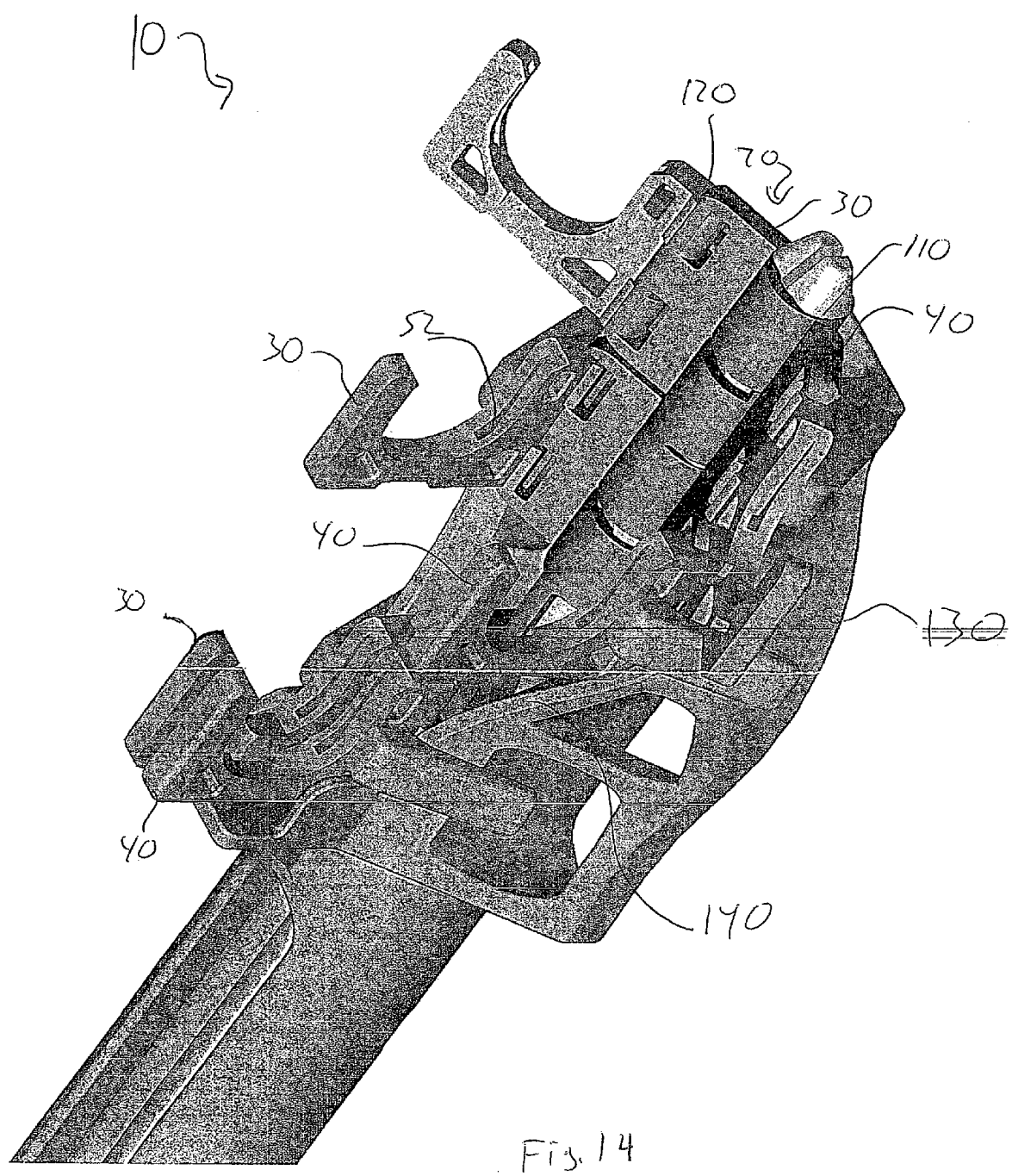
FIG. 14 provides a perspective view of an assembly showing a clamp portion in several stages of actuation in accordance with an embodiment of the invention.

The various embodiments of assemblies 10 discussed herein can be actuated by any suitable manner, such as by an actuator 130. The dual plane clamp assemblies shown in FIGS. 11 and 12 can be actuated by an actuator 130 having a guide 140, as shown in FIGS. 13 and 14. For example, the guide can be moved longitudinally about the assembly 10 so that the guide 140 interacts with the first and second clamp portions 30, 40 to move them towards each other. The guide 140 can move the first and second clamp portions 30, 40 towards each other until they have been moved together completely, (e.g., the pins 80 of one joinable part being engaged with the corresponding receiving apertures 90 in the opposite joinable part). In the embodiment of FIG. 13, guide 140 includes a first curved surface 142 adapted to orientate first and second joinable parts parallel to each other. A second curved surface 144 is provided to translate the first and second joinable portions towards each other after they are parallel. FIG. 14 shows an embodiment of this type of action. FIG. 14 shows the clamps 30 and 40 in three different positions along the actuator 130. In the first position, the clamps 30 and 40 are not engaged with the guide 140 and remain open and nonparallel. In the second position, the clamps are engaged with the guide and are oriented parallel to each other. In the third position, the clamps have been moved together.

Figure 15:
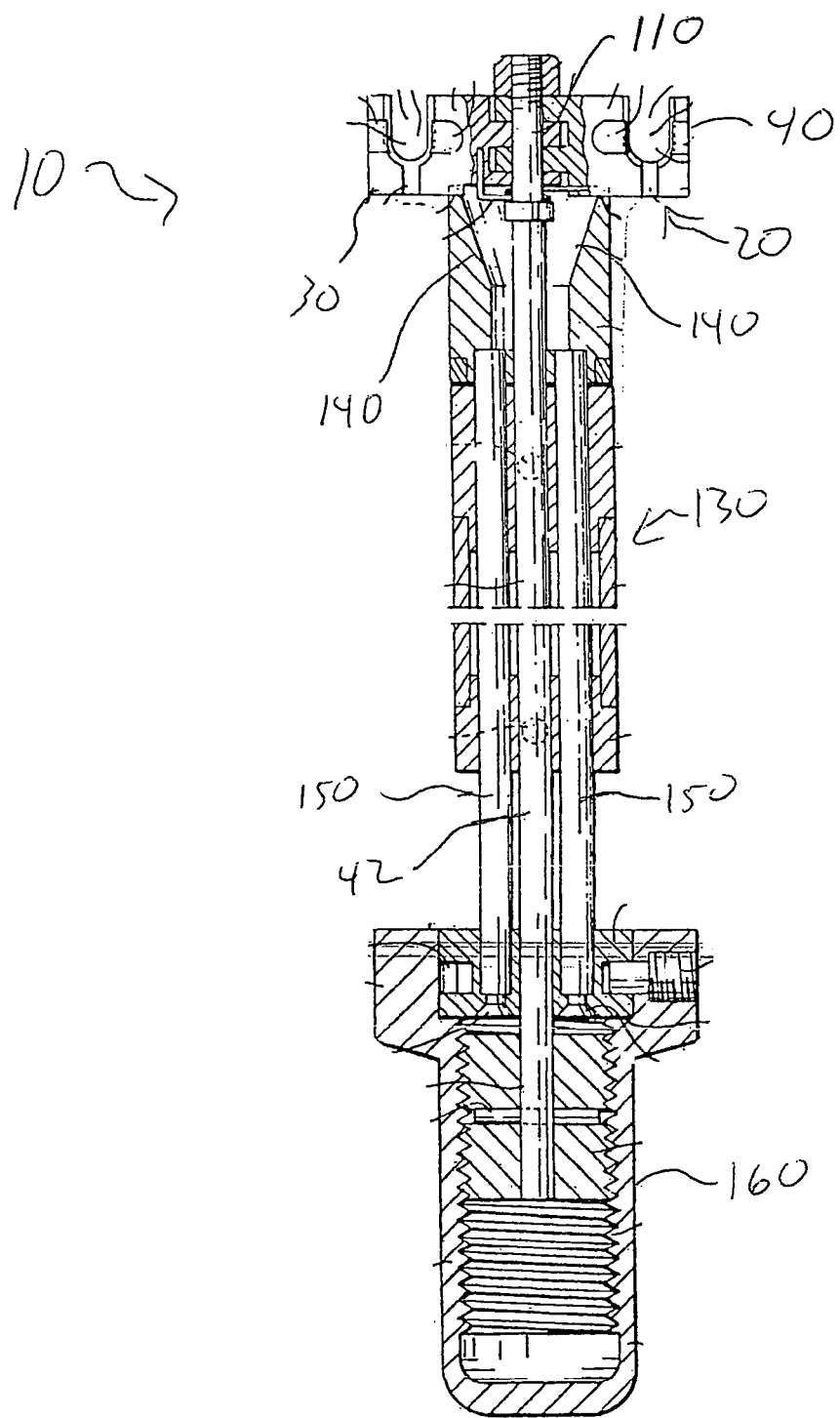
FIG. 15 provides a plan view of an actuator in accordance with an embodiment of the invention.

In the embodiment of FIG. 15, the clamp 20 can also be opened and/or closed by actuation (e.g., longitudinal movement) of a guide 140 (e.g., bushing and/or cam) having a generally curved surface. In the embodiment of FIG. 15, the clamp can be closed by actuation of the guide 140. For example, the guide can be moved longitudinally about the assembly 10 so that the guide 140 interacts with the first and second clamp portions 30, 40 to move them towards each other until they have been moved together completely, (e.g., the pins 80 of one joinable part being engaged with the corresponding receiving apertures 90 in the opposite joinable part). In some embodiments, when the guide is further displaced a pusher connected with guide 140 will push the joined fastener out of the clamp, thereby leaving a joined vessel and allowing the rest of the assembly to be removed from the surgical area.

Figure 7:
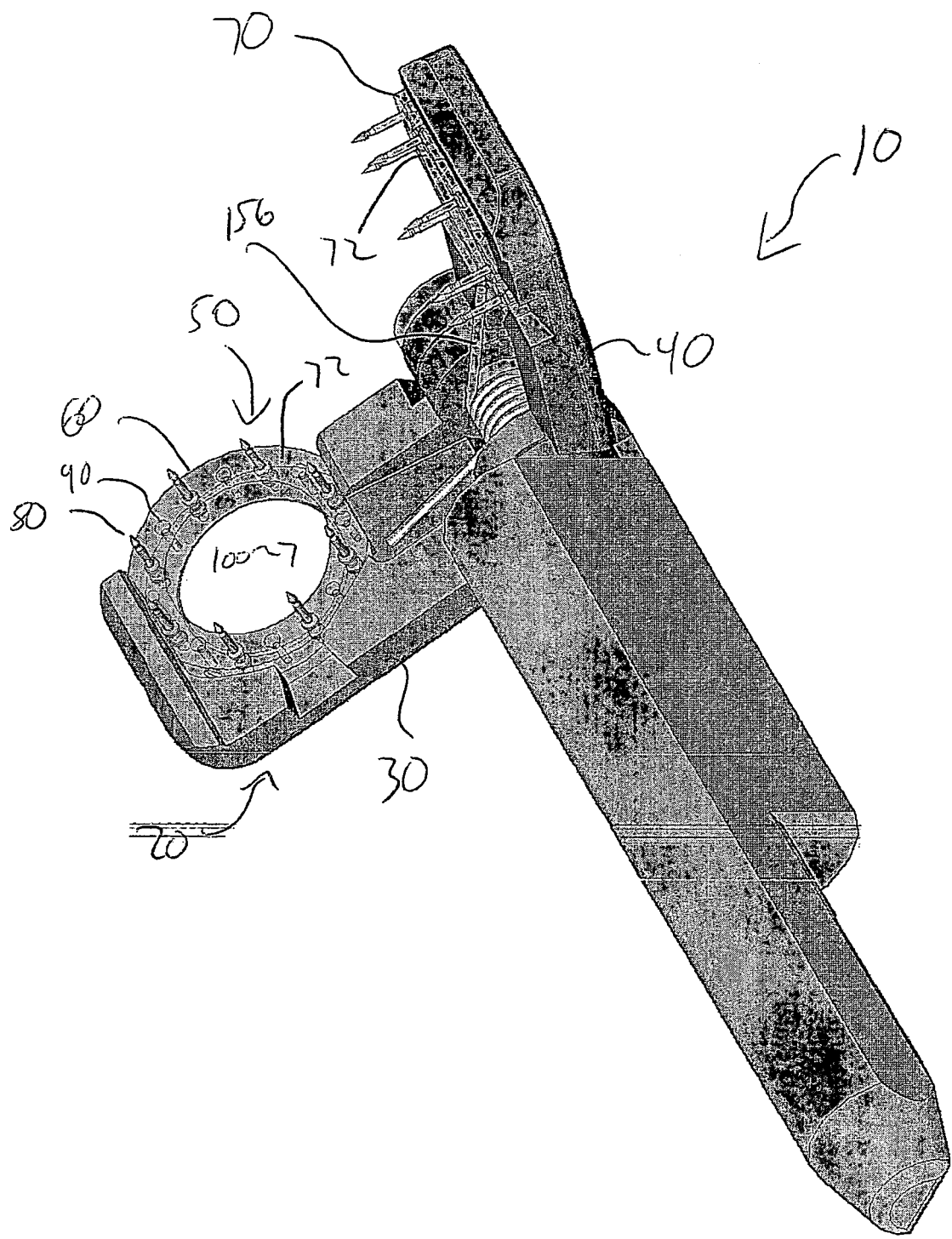
FIG. 7 provides a perspective view of an assembly in accordance with an embodiment of the invention.

In some embodiments, as shown in FIG. 15, guide 140 can be moved longitudinally by the relative movement between a carrier rod 42 and one or more guiding rods 150. In such embodiments, the first and second members of the clamp are rotatably coupled to a carrier rod 42 parallel with the longitudinal axis of the assembly. Further, one or more guide rods 150 parallel with the carrier rod 42 can be fixed to the guide 140 and a handle 160. In such embodiments, the carrier rod 42 can be threadingly engaged with the handle 160, and when the handle is turned the carrier rod is moved longitudinally relative to the guide rods 150 and guide 140. Such movement moves the guide longitudinally to interact with the clamp. A biasing member 156 (e.g. a spring), as best shown in FIG. 7, may be provided to bias the clamp portions away from each other.

The invention also includes methods of using and making any of the various assemblies discussed herein. In use, for example, an end of a vessel can be threaded through an aperture within a first joinable part of a fastener. Another end of a vessel can be threaded through a second joinable part of the fastener. Each vessel end can then be anchored to its respective joinable part by directing pins carried by the joinable part through the vessel. The joinable part can be received within the clamp before or after the vessel is threaded and anchored. The assembly can then be activated to move the two joinable parts towards each other. In some embodiments, the assembly is adapted to facilitate the alignment of the joinable parts as described herein. Once the joinable parts meet, the pins of one joinable part can align with the receiving holes of the opposite joinable part. Continued actuation of the assembly will cause the joinable parts to join and the anastomosis will be complete. The fastener can then be removed from the clamp and the assembly can be removed from the surgical area.

Numerous characteristics and advantages of the invention covered by this document have been set forth in the foregoing description. It will be understood, however, that this disclosure is, in many respects, only illustrative. Changes can be made in details, particularly in matters of shape, size and ordering of steps without exceeding the scope of the invention. The invention's scope is, of course, defined in the language in which the appended claims are expressed.

What is claimed is:

1. An assembly for anastomosis comprising a clamp and a fastener having first and second joinable parts carried by the clamp, the joinable parts providing respective opposing faces providing apertures and corresponding pins for use in joining the opposing faces,
   the assembly being adapted to facilitate the alignment of the first and second joinable parts, and in turn, alignment of respective apertures and pins,
   wherein the clamp holds the first and second joinable parts at an oblique angle relative to the clamp and the oblique angle is configured such that the opposing faces are positioned substantially parallel to each other when the tips of the pins first contact their corresponding apertures.

2. An assembly according to claim 1, wherein the clamp comprises a hinge portion adapted to permit the parts to be initially held and positioned in an open and non-parallel relationship, and to thereafter permit the joinable parts to be engaged, at the anastomotic site, in a substantially parallel relationship.

3. An assembly according to claim 1, wherein the clamp includes a clamp portion plane and one or more of the joinable parts includes a joinable part plane, further defining an angle between the clamp portion plane and the joinable part plane, the angle being more than about one degree.

4. An assembly according to claim 1 wherein the assembly further includes an actuator.

5. An assembly according to claim 1, the clamp being actuatable by a guide.

6. An assembly according to claim 1, wherein the clamp comprises a first clamp portion and a second clamp portion.

7. An assembly according to claim 1, wherein the fastener includes a pin.

8. An assembly according to claim 1, wherein the fastener includes at least eight pins.

9. An assembly according to claim 1, wherein the fastener includes a disc-type shape having a diameter of more than about 3.5 mm and a pin.

10. An assembly according to claim 1, wherein the fastener includes a disc-type shape having a diameter of more than about 4 mm and a pin.

11. An assembly according to claim 1, wherein one or more of the joinable parts comprises a generally disc-type shape and a plurality of pins and receiving apertures circumferentially disposed around the disc.

12. An assembly according to claim 1, wherein one or more of the joinable parts comprises a generally disc-type shape including a disc aperture.

13. An assembly according to claim 6 wherein each of the first and second clamp portions provide a respective clamp portion plane CPP, and each of the first and second joinable parts provide a joinable part plane JPP, and wherein the clamp portion plane CPP and the respective joinable part plane JPP are skewed relative to each other so as to facilitate alignment.

14. An assembly according to claim 13 wherein angle SA is defined as the angle between the clamp portion plane CPP and the joinable part plane JPP, and angle SA is more than about one degree.

15. An assembly according to claim 14 wherein angle SA is more than about 5 degrees.

16. An assembly according to claim 15 wherein angle SA is more than about 7 degrees.

* * * * *